US012622578B2

(12) United States Patent
Liu et al.

(10) Patent No.: US 12,622,578 B2
(45) Date of Patent: May 12, 2026

(54) LIGHTING SOURCE AND ENDOSCOPE

(71) Applicant: BEIJING WESTON ASIA-PACIFIC OPTO-ELECTRIC INSTRUMENT CO., LTD., Beijing (CN)

(72) Inventors: Xiaohua Liu, Beijing (CN); Hong Li, Beijing (CN); Xiatian Wang, Beijing (CN)

(73) Assignee: BEIJING WESTON ASIA-PACIFIC OPTO-ELECTRIC INSTRUMENT CO., LTD., Beijing (CN)

( * ) Notice: Subject to any disclaimer, the term of this patent is extended or adjusted under 35 U.S.C. 154(b) by 903 days.

(21) Appl. No.: 17/907,073

(22) PCT Filed: Mar. 24, 2021

(86) PCT No.: PCT/CN2021/082693
§ 371 (c)(1),
(2) Date: Sep. 22, 2022

(87) PCT Pub. No.: WO2021/190554
PCT Pub. Date: Sep. 30, 2021

(65) Prior Publication Data
US 2023/0218153 A1      Jul. 13, 2023

(30) Foreign Application Priority Data

Mar. 25, 2020   (CN) .......................... 202010216848.3
Mar. 25, 2020   (CN) .......................... 202020392837.6

(51) Int. Cl.
*G02B 23/26*      (2006.01)
*A61B 1/00*      (2006.01)
(Continued)

(52) U.S. Cl.
CPC ........ *A61B 1/0684* (2013.01); *A61B 1/00105* (2013.01); *A61B 1/0607* (2013.01);
(Continued)

(58) Field of Classification Search
CPC . A61B 1/0684; A61B 1/0676; A61B 1/00105; A61B 1/0607; G02B 23/2461
See application file for complete search history.

(56) References Cited

U.S. PATENT DOCUMENTS

2006/0058584 A1*   3/2006   Hirata .................. A61B 1/0684
600/179

FOREIGN PATENT DOCUMENTS

CN          105407790 B          10/2018
CN          110058400 A          7/2019
(Continued)

OTHER PUBLICATIONS

Liu et al.; CN110531511A; Sep. 18, 2025; Machine translation into English (Year: 2019).*

*Primary Examiner* — Ryan D Howard
(74) *Attorney, Agent, or Firm* — MLO, a professional corp.

(57) ABSTRACT

A lighting source and an endoscope are provided, and the lighting source is used for the endoscope. The lighting source includes a light-emitting diode (LED) chip and a substrate; the LED chip is arranged on and fixedly connected to the substrate, and is packaged into the lighting source; and the lighting source is circular ring-shaped or arc-shaped. The endoscope includes an endoscope tube; an objective lens, located at one end of the endoscope and at least partially located inside the endoscope tube; and the lighting source.

15 Claims, 5 Drawing Sheets

(51) Int. Cl.

| | | |
|---|---|---|
| *A61B 1/06* | (2006.01) | |
| *F21V 9/40* | (2018.01) | |
| *F21V 19/00* | (2006.01) | |
| *F21Y 115/10* | (2016.01) | |

(52) U.S. Cl.

CPC .............. *A61B 1/0676* (2013.01); *F21V 9/40* (2018.02); *F21V 19/002* (2013.01); *F21Y 2115/10* (2016.08)

(56) References Cited

FOREIGN PATENT DOCUMENTS

| | | | |
|---|---|---|---|
| CN | 110531511 | A | 12/2019 |
| CN | 212031852 | U | 11/2020 |
| WO | 2017012192 | A1 | 1/2017 |

* cited by examiner

LIGHTING SOURCE AND ENDOSCOPE

The present application claims the priority of Chinese patent application No. 202010216848.3 filed on Mar. 25, 2020 and Chinese patent application No. 202020392837.6 filed on Mar. 25, 2020, and the contents disclosed in the above-mentioned Chinese patent applications are incorporated herein by reference as part of the present application.

TECHNICAL FIELD

The present disclosure relates to a lighting source and an endoscope.

BACKGROUND

Rigid endoscope is an optical instrument for diagnosis and treatment, which can be inserted into a body cavity and organs of a human for direct observation. Because the rigid endoscope can obtain clear and accurate pictures of tissues and improve the accuracy of diagnosis, it possesses high application value. Disposable rigid endoscope can avoid cross infection, with the key point of reducing the manufacturing cost while ensuring the image quality.

SUMMARY

At least one embodiment of the present disclosure provides a lighting source for an endoscope, wherein the lighting source comprises a light-emitting diode (LED) chip and a substrate; the LED chip is arranged on and fixedly connected to the substrate, and is packaged into the lighting source; and the lighting source is circular ring-shaped or arc-shaped.

In some examples, the lighting source is used for a disposable rigid endoscope.

In some examples, at least two LED chips are arranged on the substrate, and the at least two LED chips and the substrate are packaged into a circular ring-shaped or arc-shaped package.

In some examples, the lighting source further includes a wire connected between the at least two LED chips, the wire is routed on the substrate to connect the LED chips and is packaged in the package.

In some examples, the substrate is coated with a fluorescent glue for packaging.

In some examples, a circuit connection mode between the LED chips is a series connection mode, a parallel connection mode or a series-parallel hybrid connection mode.

In some examples, the circuit connection mode between the LED chips comprises: the LED chips comprise a plurality of LED chipsets, the LED chips in each of the plurality of LED chipsets are connected in series, and the plurality of LED chipsets are connected in parallel; or, the LED chips comprise a plurality of LED chipsets, the LED chips in each of the plurality of LED chipsets are connected in parallel, and the plurality of LED chipsets are connected in series.

In some examples, an edge of an outer surface of an objective lens of the endoscope is provided with a groove for mounting the lighting source.

In some examples, the groove is circular ring-shaped; at least one arc-shaped lighting source is mounted in the groove; or, a circular ring-shaped lighting source is mounted in the groove.

In some examples, the groove is arc-shaped; at least one arc-shaped lighting source is mounted in the groove.

In some examples, the groove is sealed by adopting a protective sheet.

In some examples, the lighting source is mounted on an edge of a surface of an objective lens.

At least one embodiment of the present disclosure provides an endoscope, comprising: an endoscope tube; an objective lens, located at one end of the endoscope and at least partially located inside the endoscope tube; and the lighting source as described in any of the above, located at the end of the endoscope tube where the objective lens is provided.

In some examples, an edge of an outer surface of the objective lens is provided with a groove for mounting the lighting source.

In some examples, when viewed from an axial direction of the endoscope tube, the groove is circular ring-shaped or arc-shaped to accommodate the lighting source.

In some examples, the groove is delimited by a partial surface of the objective lens and a partial surface of an inner wall of the endoscope tube, and a side wall of the groove opposite to the endoscope tube is coated with a light-shielding material.

In some examples, the groove is circular ring-shaped; at least one arc-shaped lighting source is mounted in the groove; or, one circular ring-shaped lighting source is mounted in the groove.

In some examples, a plurality of arc-shaped lighting sources are uniformly arranged in the groove.

In some examples, the groove is arc-shaped; and at least one arc-shaped lighting source is mounted in the groove.

In some examples, the edge of the outer surface of the objective lens is uniformly provided with a plurality of arc-shaped grooves, and one arc-shaped lighting source is mounted in each of the plurality of arc-shaped grooves.

In some examples, an opening of the groove is provided with a protective sheet to seal the lighting source.

In some examples, the lighting source is mounted on an outer surface of the objective lens and is located at an edge of the outer surface.

In some examples, a side surface of the objective lens facing an inner wall of the endoscope tube is provided with a groove for mounting the lighting source.

In some examples, the objective lens comprises an inner surface, the inner surface faces an end of the endoscope tube opposite to the end where the objective lens is provided, and an edge of the inner surface is provided with a groove for mounting the lighting source.

In some examples, the endoscope is a disposable rigid endoscope or an electronic endoscope.

In some examples, a minimum inner diameter of the endoscope tube is 3.8 mm, a minimum outer diameter of the endoscope tube is 4.0 mm, and a minimum dimension of the lighting source along a radial direction of the endoscope tube is 0.5 mm.

In some examples, a minimum inner diameter of the endoscope tube is 2.7 mm, a minimum outer diameter of the endoscope tube is 2.9 mm, and a minimum dimension of the lighting source along a radial direction of the endoscope tube is 0.3 mm.

BRIEF DESCRIPTION OF THE DRAWINGS

In order to more clearly illustrate the technical solutions of the embodiments of the present disclosure, the drawings of the embodiments will be briefly described in the following; it is obvious that the described drawings are only related to some embodiments of the present disclosure and thus are not limitative to the present disclosure.

DETAILED DESCRIPTION

In order to make objects, technical details and advantages of the embodiments of the disclosure apparent, the technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the invention.

Figure 1:
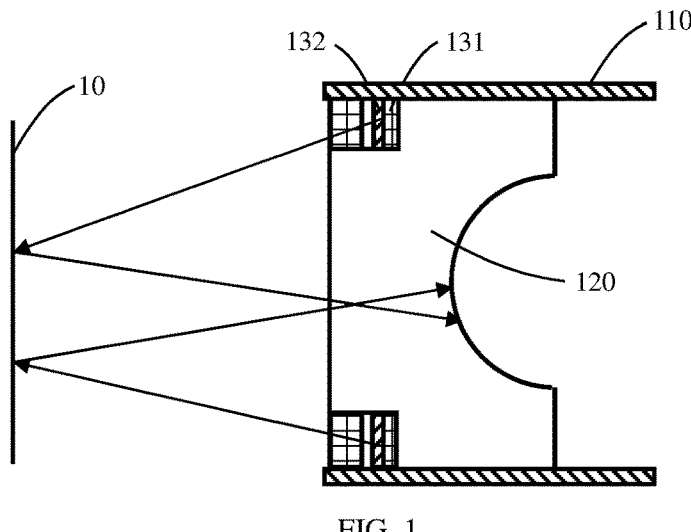
FIG. 1 is a partial cross-sectional view of a rigid endoscope.

FIG. 1 is a partial cross-sectional view of a rigid endoscope. As illustrated in FIG. 1, the rigid endoscope can extend into a body cavity and organs of a human, and image the body cavity and a tissue surface 10 of the organs. The rigid endoscope includes an outer endoscope tube 110, and an objective lens 120 which is mounted in the outer endoscope tube 110 and located at an end of the outer endoscope tube 110. The rigid endoscope may further include a lighting source for illuminating the tissue surface 10 to obtain a clear image of the tissue surface 10.

Figure 2:
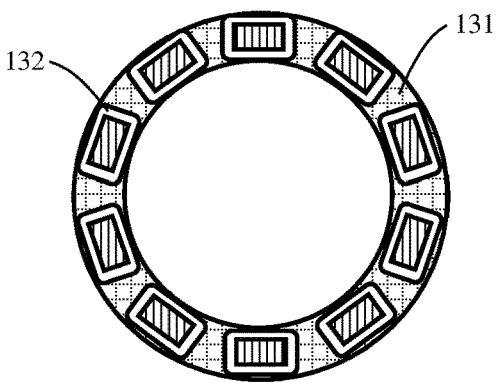
FIG. 2 is a schematic diagram of a lighting source.

FIG. 2 is a schematic diagram of a lighting source. As illustrated in FIGS. 1 and 2, LED beads 132 can be used as the lighting source, and a plurality of LED beads 132 can be arranged and attached onto a circuit board 131. For example, the LED beads 132 can be attached onto the circuit board 131 by utilizing SMT (Surface Mounting Technology). In such an LED bead 132, a single LED chip is packaged to form an LED bead. Because each LED bead 132 is obtained by packaging a LED chip and because the packaged LED bead 132 has a large size, the number of the LED beads 132 that can be attached in a certain space is limited. For example, for a rigid endoscope with a diameter of 4 mm, generally only about ten LED beads 132 can be mounted therein. Therefore, in the case where the method of mounting LED beads onto a circuit board is adopted, the number of the LED beads that can be arranged in the rigid endoscope will be small, the number of the LED chips and other light-emitting elements will be small, and the illumination brightness will be limited, which will affect the imaging definition. Moreover, if the LED beads that are used as surface-mounted light sources are connected in series, the mounting process will be laborious. Under the circumstance that the voltage of each LED bead is about 3.1V, when the number of the LED beads is more than ten, the total voltage of the circuit is excessively large, which is not conductive to be used inside a human body.

In view of this, embodiments of the present disclosure provide a lighting source of a disposable rigid endoscope to solve at least one of the problems involved in the traditional surface-mounted LED bead, including small number of beads that can be arranged, low brightness, difficult mounting, high total voltage and the like.

The embodiment of the present disclosure provides a lighting source for a rigid endoscope and a rigid endoscope including the lighting source. The lighting source can improve the space utilization rate so that more light-emitting elements can be arranged in a certain space to increase the light-emitting area, thereby obtaining higher illumination brightness and improving the resolution of the images as captured.

Hereinafter, embodiments of the present disclosure will be explained in details with reference to the accompanying drawings. It should be noted that the same reference numeral in different figures will be used for indicating the same element having been described.

Figure 8:
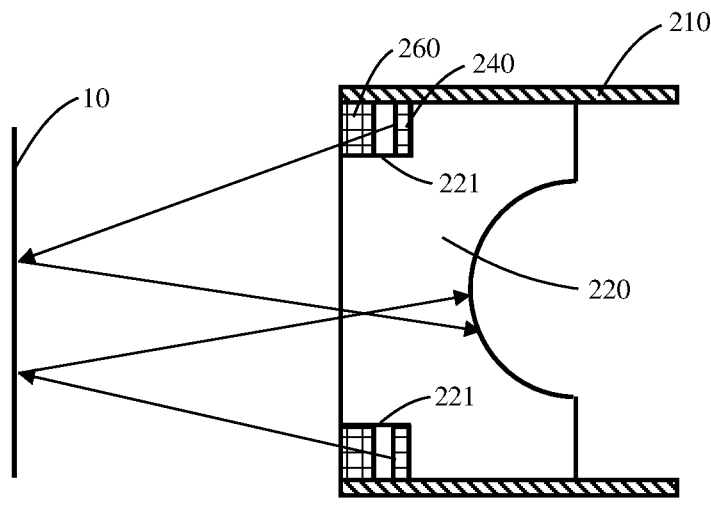
FIG. 8 is a partial cross-sectional view of a rigid endoscope provided by some embodiments of the present disclosure.

The lighting source for disposable rigid endoscope in the present disclosure adopts an LED lighting source 240. As illustrated in FIG. 8, an objective lens 220 is mounted inside an outer endoscope tube 210; the LED lighting source 240 of the present disclosure is arranged on a surface of the objective lens 220 facing the tissue surface 10 of the objective lens, and is located in a groove formed at an edge of the objective lens 220. At a side of the groove facing the tissue surface 10 of the objective lens, a protective sheet 260 is mounted above the LED lighting source 240 to seal the groove, so as to protect the LED lighting source 240.

Figure 9:
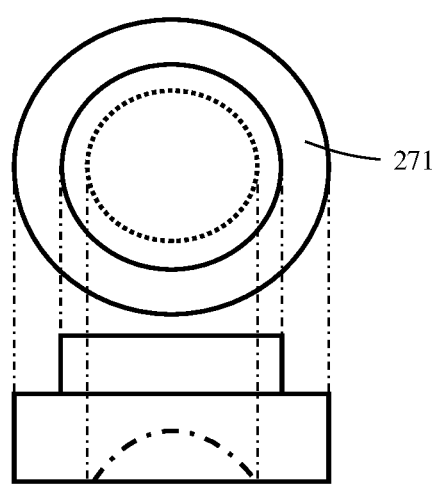
FIG. 9 is a schematic structural diagram of an objective lens manufactured with a circular ring-shaped groove provided by some embodiments of the present disclosure.
Figure 11:
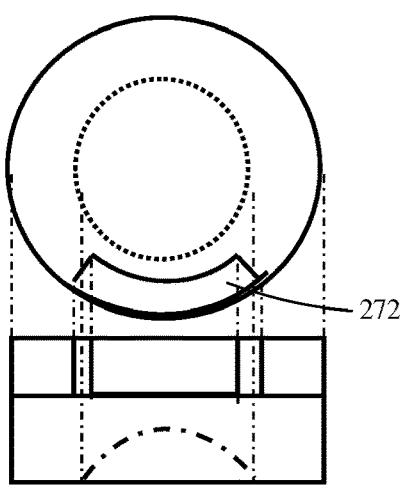
FIG. 11 is a schematic structural diagram of an objective lens manufactured with an arc-shaped groove provided by some embodiments of the present disclosure.

A bottom contour of the groove in the objective lens can be circular ring-shaped or arc-shaped. As illustrated in FIG. 9, it is a groove formed at the edge of the objective lens and has a circular-shaped outer contour. The objective lens 220 in this form can be matched and used with a single LED lighting source having an annular-shaped edge contour, or can be matched and used with a plurality of LED lighting sources each having an arc-shaped edge contour; and it can also be matched and used with a single annular-shaped LED lighting source. The groove illustrated in FIG. 11 is formed at the edge of the objective lens and has an arc-shaped outer contour; and depending on the shape of the groove, an arc-shaped LED lighting source matched therewith can be used.

Alternatively, the LED lighting source 240 can also be directly mounted on the edge of the surface of the objective lens 220, so that a groove can be omitted.

The above-described LED lighting source includes LED chips 242 connected in series, the total circuit voltage is the sum of the voltage values of all these LED chips 242, and the total circuit current is equal to the current value of each of these LED chips 242. Alternatively, the LED chips are connected in parallel, the total circuit voltage is the voltage of each of these LED chips, and the total circuit current is the sum of the current values of all these LED chips.

The above-described LED lighting source includes LED chips 242 connected in series to form an LED chipset 250, and a plurality of LED chipsets 250 are connected in parallel. Alternatively, LED chips 242 are connected in parallel to form an LED chipset 250, and a plurality of LED chipsets 250 are connected in series to form an LED lighting source.

Figure 7:
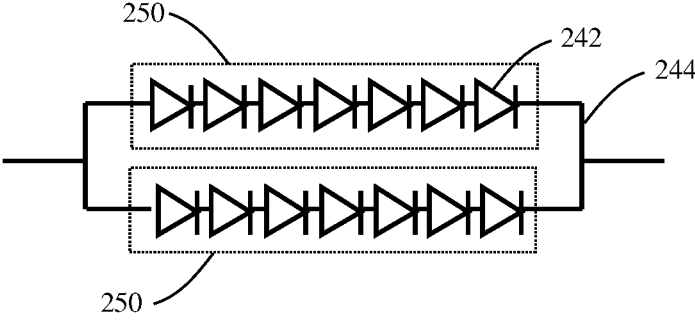
FIG. 7 is a schematic diagram illustrating circuit connections of a lighting source provided by some embodiments of the present disclosure.

The number of the above-described LED chipsets 250 and the number of the above-described LED chips 242 are set according to the groove contour and the actual voltage and current. FIG. 7 illustrates an embodiment of the present disclosure, in which seven LED chips 242 are connected in series to form a chipset. The voltage of the LED chipset 250 is the sum of the voltage values of all the LED chips 242, and the current of the LED chipset is equal to the current value of each of these LED chips 242. When LED chipsets 250 are connected in parallel, the total voltage of the LED circuit is equal to the voltage of each LED chipset 250, and the total current of the LED circuit is the sum of the current values of all the LED chipsets 250. The number of the LED chips in the LED lighting source is more than the number of the LED chips in the surface-mounted LED beads 132. A series-parallel combined connection mode is adopted to ensure that the overall voltage of the circuit will not be increased.

Figure 4:
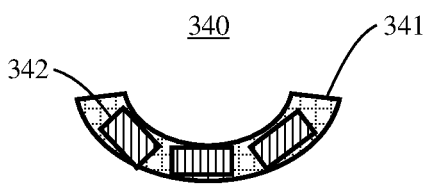
FIG. 4 is a schematic diagram of a lighting source provided by some embodiments of the present disclosure.

According to actual requirements, the outer contour of the LED lighting source can be arc-shaped. Referring to FIG. 4, an LED lighting source according to an embodiment of the present disclosure is illustrated. In the figure, a single LED bead made from three LED chips 242 by die bonding is illustrated by way of example. According to actual requirements and the shape of the groove, the arc shape of the LED lighting source and the number of the LED chips 242 are adjusted, and the circuit connection among these LED chips 242 is a series connection, a parallel connection or a combination thereof.

The basic manufacturing process of the LED light source 7 will be described below.

Die bonding: sequentially attaching LED chips 242 onto a substrate 241 to be arranged evenly on the substrate 241 through an adhesive glue, and then baking the adhesive glue for a baking time set according to the properties of the adhesive glue as selected.

Wire bonding: sequentially connecting the LED chips 242, and connecting the LED chips 242 with a power supply, through metal leads and conductive lines on the substrate 241 to form an electrical circuit.

Adhesive dispensing: coating a fluorescent glue 243 onto the substrate 241 for packaging, and baking the fluorescent glue 243 to obtain the LED lighting source 240.

Hereinafter the technical solution of the present disclosure will be further explained in details in conjunction with some exemplary embodiments of the present disclosure.

Figure 3:
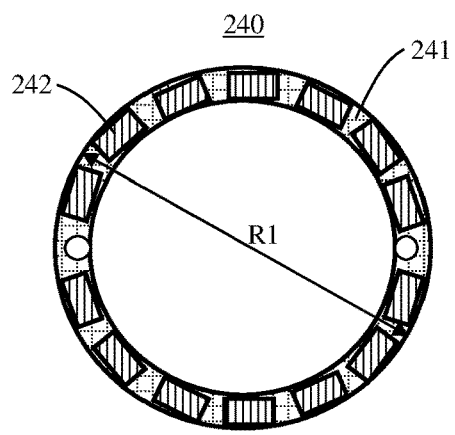
FIG. 3 is a schematic diagram of a lighting source provided by some embodiments of the present disclosure.

FIG. 3 is a schematic diagram of a lighting source provided by some embodiments of the present disclosure. As illustrated in FIG. 3, the lighting source 240 includes LED chips 242 and a substrate 241. The LED chips 242 are arranged on and fixedly connected to the substrate 241, and then the LED chips 242 and the substrate 241 are packaged to form the lighting source. The lighting source is circular ring-shaped or arc-shaped, and FIG. 3 illustrates the distribution of the LED chips on a circular ring-shaped substrate. The circular ring-shaped or arc-shaped lighting source can surround the edge of the circular-shaped objective lens without hindering the light reflected at the tissue surface from entering the objective lens.

According to the embodiment of the present disclosure, each of the LED chips can be connected onto the substrate, and all the LED chips on the substrate can be entirely packaged to form a circular ring-shaped or arc-shaped lighting source. Due to the small size of the LED chips, more LED chips can be arranged in a certain space on the substrate as compared with the above-mentioned method of attaching the LED beads onto the substrate, thereby reducing the distance between adjacent LED chips, and hence obtaining higher illumination brightness and improving the resolution of the images as captured.

For example, the lighting source can be used for disposable rigid endoscopes. Rigid endoscope is a kind of endoscope, which can also be referred to as hard-tube endoscope. Disposable rigid endoscope can avoid cross infection. The endoscope tube of the disposable rigid endoscope has an outer diameter of, for example, 4 mm, and an inner diameter of, for example, 3.8 mm. In such rigid endoscope, the smallest dimension of the lighting source in the radial direction of the endoscope tube is 0.5 mm. In some other embodiments, the outer diameter of the disposable rigid endoscope is, for example, 2.9 mm, and the inner diameter is 2.7 mm, for example. In such rigid endoscope, the smallest dimension of the lighting source in the radial direction of the endoscope tube is 0.3 mm. Of course, the embodiment according to the present disclosure is not limited to this, and other sizes can be used for the outer diameter and inner diameter of the rigid endoscope. However, when the inner diameter of the rigid endoscope is as low as 3.8 mm or further, as low as 2.7 mm, the mounting position of the lighting source is very limited, and the lighting source according to the present disclosure can provide sufficient brightness in a limited space.

For example, at least two LED chips are arranged on the substrate, and the at least two LED chips and the substrate form a circular ring-shaped or arc-shaped package, which can be used as a lighting source. For example, the package can be understood as an LED bead, which is equivalent to improving the structure and shape of the traditional LED bead, so that the improved LED bead contains a plurality of closely adjacent LED chips, and the whole LED bead is circular ring-shaped or arc-shaped. Compared with the traditional LED bead, the number of the LED chips arranged in a limited space is increased, thus the illumination brightness is improved, and the outer contour of the LED bead is more matched with the shape of the rigid endoscope. For example, the LED chip may be a semiconductor die.

For example, the substrate may have a circular ring shape, and the at least two LED chips are arranged in an annular shape. As illustrated in FIG. 3, for example, fourteen LED chips can be uniformly distributed along a circumferential direction on the circular ring-shaped substrate with the outer diameter R1, and the circular ring-shaped substrate and the fourteen LED chips can be packaged into a circular ring-shaped package which can be used as a circular ring-shaped lighting source 240.

Alternatively, the substrate may have an arc shape, and the at least two LED chips are arranged in an arc shape. FIG. 4 is a schematic diagram of another lighting source provided by some embodiments of the present disclosure, illustrating the distribution of the LED chips on an arc-shaped substrate. As illustrated in FIG. 4, in the case that the substrate is arc-shaped, several LED chips can be arranged on the substrate along an arc shape, and the arc-shaped substrate and the several LED chips can be packaged into an arc-shaped package which can be used as an arc-shaped lighting source 340. In FIG. 4, a single LED bead made from three LED chips 342 by die bonding is illustrated by way of example; that is to say, three LED chips 342 are arranged on the substrate 341. In actual usage, the arc shape of the LED lighting source and the number of the LED chips included in the lighting source can be adjusted according to actual requirements and the groove shape of the objective lens.

For example, a single circular ring-shaped lighting source, or one or more arc-shaped lighting sources can be arranged at the edge of the objective lens.

For example, the lighting source further includes wires connected among the at least two LED chips. These wires are routed on the substrate and packaged into the package. For example, FIG. 7 illustrates wires 244 for connecting the LED chips, and these wires 244 can be routed on the substrate for connecting the LED chips arranged on the substrate.

For the embodiments illustrated in FIGS. 1 and 2, it is necessary to route complex connecting wires on the circuit board to electrically connect the LED beads. However, in the present embodiment, a package formed by packaging wires among a plurality of LED chips, the plurality of LED chips and the substrate into a whole can be used as an independent lighting device. It's equivalent to that one or more LED beads can be directly used in the rigid endoscope for illumination, which is effected upon the power being turned on. There is no need of considering the problems involved in assembling the LED beads with the circuit board or the problems involved in routing the wires on the circuit board as illustrated in FIGS. 1 and 2, which solves the problem of difficult process of assembling the lamp beads with the circuit board and the problem of complicated wire-routing in the circuit board area, thereby improving the product yield and hence reducing the cost.

Figure 5:
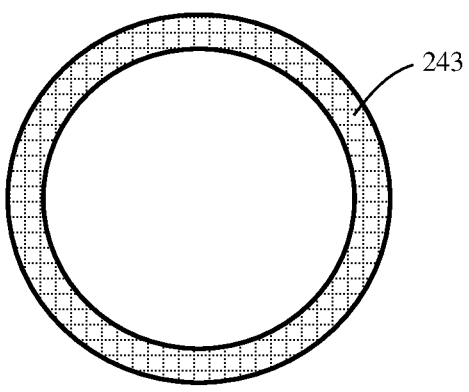
FIG. 5 is a schematic front view of a lighting source provided by some embodiments of the present disclosure.
Figure 6:
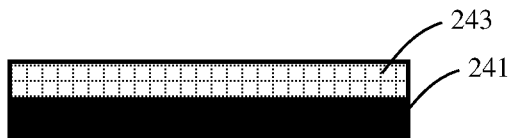
FIG. 6 is a schematic top view of a lighting source provided by some embodiments of the present disclosure.

FIG. 5 is a schematic front view of another lighting source provided by some embodiments of the present disclosure, and FIG. 6 is a schematic cross-sectional view of another lighting source provided by some embodiments of the present disclosure. As illustrated in FIGS. 5 and 6, the packaging can be achieved by coating a fluorescent glue 243 on the substrate 241. For example, the lighting source can be prepared by the following steps (1) to (3).

(1) Die bonding: sequentially attaching several LED chips onto a substrate to be arranged evenly on the substrate through an adhesive glue, and then baking the adhesive glue, in which the baking time can be set according to the properties of the adhesive glue as selected.

(2) Wire bonding: sequentially connecting the LED chips, and connecting the LED chips with a power supply, through metal leads and conductive lines on the substrate to form an electrical circuit. Among them, the power supply can be arranged at an end of the rigid endoscope away from the objective lens, and the power supply can be connected with an electrode of the lighting source by using a lead wire. Alternatively, the power supply can be arranged on the substrate.

(3) Adhesive dispensing: coating a fluorescent glue onto the substrate for packaging, and baking the fluorescent glue to form the lighting source.

For example, the circuit connection between the LED chips is series connection, parallel connection, or series-parallel hybrid connection.

For the embodiment illustrated in FIGS. 1 and 2, if the LED beads are connected in series for use, when the voltage of each LED bead is about 3.1V and there are more than ten LED beads, the total voltage of the circuit will be excessively large, which is not conducive to be used inside a human body. Therefore, in the present embodiment, the total voltage of the lighting source is lower than a voltage threshold (e.g., 15 V) by adopting one of series connection mode, parallel connection mode or series-parallel hybrid connection mode, which conforms to the safety threshold for use inside the human body and reduces the usage risk. Moreover, it also can enable the total current of the lighting source to be lower than a current threshold, for example, 20 mA.

If the series connection mode is adopted, the total circuit voltage of the lighting source is the sum of the voltage values of all the LED chips, and the total circuit current is equal to the current value of each LED chip. This mode can realize a small circuit current. In the case where the number of the LED chips is smaller than a certain threshold, the series connection mode can be adopted to ensure that the overall current and the overall voltage of the circuit are both small.

If the parallel connection mode is adopted, the total circuit voltage of the lighting source is equal to the voltage value of each LED chip, and the total circuit current is the sum of the current values of all the LED chips. This mode can realize a small circuit voltage. In the case where the number of the LED chips is smaller than a certain threshold, the parallel connection mode can also be adopted to ensure that the overall current and the overall voltage of the circuit are both small.

There are two kinds of circuit connection modes for the series-parallel hybrid connection mode. The first circuit connection mode is that, the LED chips are divided into LED chipsets, and the LED chips in each LED chipset are connected in series, so as to form a plurality of LED chipsets; each LED chipset is formed by connecting at least two LED chips in series, and the plurality of LED chipsets are connected in parallel. The second circuit connection mode is that, the LED chips are divided into LED chipsets, and the LED chips in each LED chipset are connected in parallel, so as to form a plurality of LED chipsets; each LED chipset is formed by connecting at least two LED chips in parallel, and the plurality of LED chipsets are connected in series.

FIG. 7 is a schematic diagram of circuit connections provided by some embodiments of the present disclosure, illustrating the case of serial-parallel hybrid connection mode of LED chips. As illustrated in FIG. 7, in the case that the number of the LED chips is fourteen, for example, every seven LED chips 242 can be connected in series to form an LED chipset 250, the voltage of the LED chipset 250 is the sum of the voltage values of the seven LED chips 242, and the current of the LED chipset 250 is equal to the current value of each LED chip 242. The two LED chipsets 250 can be connected in parallel, and the total voltage of the parallel circuit of the LED chip sets is equal to the voltage value of each LED chipset, and the total current of the LED circuit is the sum of the current values of the two LED chipsets 250. By using the lighting source as illustrated in FIG. 3, although the number of the LED chips is increased as compared with the case of attaching the LED beads, the overall voltage of the circuit will not be increased due to the combined use of series and parallel connections.

In the case where the number of the LED chips is greater than a certain threshold, the series-parallel hybrid connection mode can be adopted. By adjusting the number of the LED chipsets and the number of the LED chips contained in each LED chipset, the voltage and current of the circuit can meet the requirements, and can be kept in a small numerical range which is in line with the safety threshold for use inside human body.

The number of the LED chipsets and the number of the LED chips contained in each LED chipset can be set according to the contour of the space used for accommodating the lighting source in the rigid endoscope, the target voltage and the target current. The space used for accommodating the lighting source can refer to, for example, a groove formed in the objective lens.

FIG. 8 is a partial cross-sectional view of a rigid endoscope provided by some embodiments of the present disclosure. As illustrated in FIG. 8, an edge of outer surface of the objective lens 220 of the rigid endoscope is provided with a groove for mounting the lighting source 240 therein. For example, the outer surface of the objective lens 220 refers to the surface facing the outside of the endoscope tube. The objective lens 220 is mounted in the outer endoscope tube 210 and located at an end of the outer endoscope tube 210. For example, the objective lens 220 may be at least partially located in the outer endoscope tube 210. The objective lens 220 has an outer surface, an inner surface and a side surface; wherein the side surface may refer to the circumferential surface facing the inner wall of the outer endoscope tube 210; the outer surface may refer to the surface facing the tissue surface 10; the inner surface is opposite to the outer surface, and the inner surface may refer to the surface facing the other end of the outer endoscope tube 210, wherein the "other end" is opposite to the end where the objective lens 220 is located. The lighting source 240 can be arranged on the surface of the objective lens facing the tissue surface 10, that is, arranged on the outer surface, and can be located in a groove formed at the edge of the outer surface of the objective lens.

For example, an opening of the groove may be provided with a protective sheet to seal the lighting source. At a side of the groove facing the outer surface of the objective lens, a protective sheet 260 can be mounted above the LED lighting source to seal the groove and further protect the LED lighting source 240. The protective sheet 260 can be made of transparent glass, and the thickness of the protective sheet 260 is smaller than 0.3 mm, for example, to reduce the influence of the protective sheet 260 to the light transmission. For example, although the protective sheet 260 is located in the groove in the example of FIG. 8, it may also be partially located in the groove or may not be located in the groove, as long as the groove can be sealed.

For example, the side wall 221 of the groove may be coated with a light-shielding material. As illustrated in FIG. 8, the side wall 221 of the groove facing the inner wall of the outer endoscope tube 210 is coated with a light-shielding material. For example, the sidewall 221 of the groove can be coated with black paint, which can prevent the light emitted by the lighting source from diffusing into the objective lens 220.

For example, the groove can be circular ring-shaped, and at least one arc-shaped lighting source can be mounted in the groove; alternatively, a single circular ring-shaped lighting source can be mounted in the groove.

FIG. 9 is a structural diagram of an objective lens manufactured with a circular ring-shaped groove provided by some embodiments of the present disclosure. As illustrated in FIG. 9, a groove 271 is formed at the edge of the objective lens, and the outer contour of the groove 271 can be circular ring-shaped. This type of objective lens can be matched and used with a single LED lighting source having an annular-shaped edge contour, or can be matched and used with a plurality of LED lighting sources each having an arc-shaped edge contour, or can be matched and used with a single annular-shaped LED lighting source.

Figure 10:
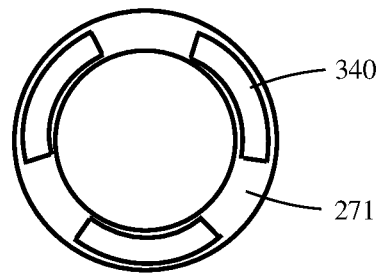
FIG. 10 is a schematic diagram illustrating an arc-shaped lighting source arranged in a circular ring-shaped groove provided by some embodiments of the present disclosure.

FIG. 10 is a schematic diagram illustrating an arc-shaped lighting source arranged in a circular ring-shaped groove provided by some embodiments of the present disclosure. As illustrated in FIG. 10, a plurality of arc-shaped lighting sources 340 can be uniformly arranged in the circular ring-shaped groove 271. For example, a corresponding number of arc-shaped lighting sources can be arranged according to the brightness requirements, and the plurality of arc-shaped lighting sources are uniformly arranged in the circular ring-shaped groove so that the light is uniformly irradiated onto the tissue surface.

For example, the groove can be arc-shaped, and at least one arc-shaped lighting source is mounted in the arc-shaped groove.

FIG. 11 is a schematic structural diagram of an objective lens manufactured with an arc-shaped groove provided by some embodiments of the present disclosure. As illustrated in FIG. 11, a groove 272 is formed at the edge of the objective lens, and the outer contour of the groove 272 is arc-shaped. According to the shape of the groove 272, an arc-shaped lighting source can be matched and used therewith.

For example, the edge of the outer surface of the objective lens can be uniformly provided with a plurality of arc-shaped grooves 272, and each arc-shaped groove is provided with a single arc-shaped lighting source, so that a plurality of arc-shaped lighting sources can be uniformly arranged at the edge of the objective lens, and the light can be uniformly irradiated onto the tissue surface.

For example, the lighting source is mounted on the outer surface of the objective lens of the rigid endoscope, and the lighting source is located at the edge of the outer surface.

Figure 12:
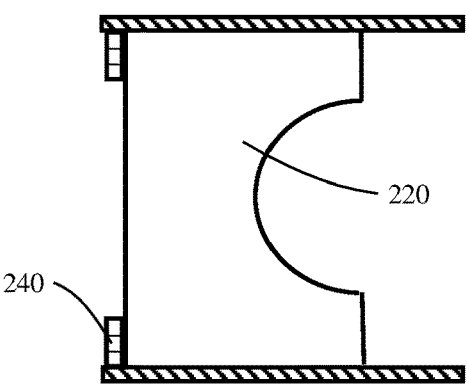
FIG. 12 is a partial cross-sectional view of a rigid endoscope provided by some embodiments of the present disclosure.

FIG. 12 is a partial cross-sectional view of another rigid endoscope according to some embodiments of the present disclosure. As illustrated in FIG. 12, the lighting source 240 can be directly mounted at the edge of the outer surface of the objective lens 220, which can avoid forming a groove in the objective lens. The exposed part of the lighting source 240 can be covered with a protective sheet, so as to play a sealing role and protect the lighting source 240 from the environment.

For example, the side surface of the objective lens of the rigid endoscope is provided with a groove for mounting the lighting source therein.

Figure 13:
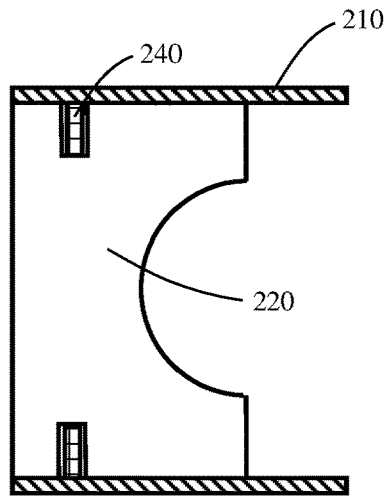
FIG. 13 is a partial cross-sectional view of a rigid endoscope provided by some embodiments of the present disclosure.

FIG. 13 is a partial cross-sectional view of another rigid endoscope according to some embodiments of the present disclosure. As illustrated in FIG. 13, a groove can be formed in the side surface of the objective lens 220, and a lighting source can be mounted in the groove of the side surface. Because the side surface of the objective lens 220 is closely attached onto the inner surface of the outer endoscope tube 210, the sealing effect of the groove can be enhanced. The distance from the groove to the outer surface of the objective lens can be smaller than a distance threshold (for example, the distance threshold is 1 mm) to reduce the influence of the objective lens to the light transmission. The groove in the side surface can be arc-shaped or circular ring-shaped, and one or more arc-shaped lighting sources can be mounted in the groove, for example.

For example, the edge of the inner surface of the objective lens of the rigid endoscope is provided with a groove for mounting the lighting source therein.

Figure 14:
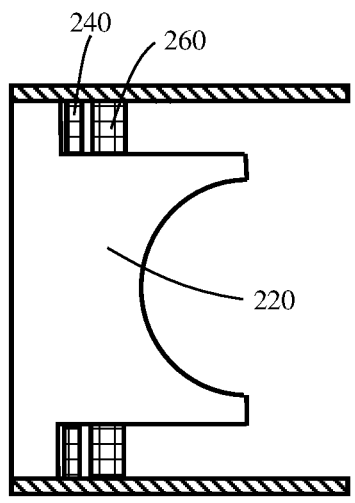
FIG. 14 is a partial cross-sectional view of a rigid endoscope provided by some embodiments of the present disclosure.

FIG. 14 is a partial cross-sectional view of another rigid endoscope according to some embodiments of the present disclosure. As illustrated in FIG. 14, a groove can be formed from the inner surface of the objective lens 220, and the lighting source 240 can be placed in the groove from the side where the inner surface is located, which can also enhance the sealing performance of the lighting source. The distance from the groove to the outer surface of the objective lens can be smaller than the distance threshold (for example, the distance threshold is 1 mm) to reduce the influence of the objective lens to the light transmission. The groove in the inner surface can be arc-shaped or circular ring-shaped, for example, and one or more arc-shaped lighting sources or a single, circular ring-shaped lighting device can be mounted in the groove. A protective sheet 260 may be provided in the groove.

The above description is made with reference to the case of a lighting source of a disposable rigid endoscope or the case of a disposable rigid endoscope by way of example, but the embodiments according to the present disclosure are not limited to this. The above-described lighting source can also be applied to other endoscopes, such as disposable or non-disposable electronic endoscopes, non-disposable rigid endoscopes, etc. An endoscope including the above-described lighting source can also be provided according to the embodiments of the present disclosure. Based on the technical effects brought by the above-described lighting source, the endoscope including such lighting source also has the same technical effects.

The embodiments of the present disclosure achieve at least one of the following beneficial effects.

1. By optimizing the shape and structure of the LED bead, the number of the LED chips that can be arranged is increased, the utilization ratio of the lamp bead in the circuit board area is improved, and a higher brightness is obtained with increased light-emitting area so that the image definition of the rigid endoscope is improved.

2. By adopting series connection, parallel connection or a combination thereof, the driving voltage can be reduced so as to meet the safety threshold for use inside the human body and reduce the usage risk.

3. By using a single LED bead or multiple LED beads as the lighting mode, the complexity of wire-routing in the circuit board area is decreased, the technological difficulty of assembling the lamp beads with the circuit board is reduced, the product yield and manufacturing efficiency are improved, and hence the cost is lowered.

It should be noted that in the above embodiments, the lighting source and the rigid endoscope are not described separately. Therefore, the structures of the lighting source according to the present disclosure and the rigid endoscope using the lighting source can be referred to each other among various embodiments. For example, the rigid endoscope can be a rigid endoscope with a single endoscope tube, that is, both the objective lens and the lighting device are located in the same endoscope tube. Moreover, other structures of the rigid endoscope are not described in detail. For example, it may further include a rod lens, eyepiece and other structures for transmitting image light.

The above are merely exemplary embodiments of the present disclosure, and are not intended to limit the scope of protection of the present disclosure, which is determined by the appended claims

What is claimed is:

1. An endoscope, comprising:
an endoscope tube;
an objective lens, located at one end of the endoscope and at least partially located inside the endoscope tube; and
a lighting source, located at the end of the endoscope tube where the objective lens is provided,
wherein the lighting source comprises a light-emitting diode (LED) chip and a substrate;
the LED chip is arranged on and fixedly connected to the substrate, and is packaged into the lighting source; and
the lighting source is circular ring-shaped or arc-shaped,
wherein the objective lens comprises an inner surface,
the inner surface faces an end of the endoscope tube opposite to the end where the objective lens is provided, and an edge of the inner surface is provided with a groove for mounting the lighting source.

2. The endoscope as claimed in claim 1, wherein at least two LED chips are arranged on the substrate, and the at least two LED chips and the substrate are packaged into a circular ring-shaped or arc-shaped package.

3. The endoscope as claimed in claim 2, wherein the lighting source further comprises a wire connected between the at least two LED chips,
the wire is routed on the substrate to connect the LED chips, and is packaged in the package.

4. The endoscope as claimed in claim 1, wherein the substrate is coated with a fluorescent glue for packaging.

5. The endoscope as claimed in claim 1, wherein a circuit connection mode between the LED chips is a series connection mode, a parallel connection mode or a series-parallel hybrid connection mode.

6. The endoscope as claimed in claim 5, wherein the circuit connection mode between the LED chips comprises:
the LED chips comprise a plurality of LED chipsets, the LED chips in each of the plurality of LED chipsets are connected in series, and the plurality of LED chipsets are connected in parallel; or,
the LED chips comprise a plurality of LED chipsets, the LED chips in each of the plurality of LED chipsets are connected in parallel, and the plurality of LED chipsets are connected in series.

7. The endoscope as claimed in claim 1, wherein, when viewed from an axial direction of the endoscope tube, the groove is circular ring-shaped or arc-shaped to accommodate the lighting source.

8. The endoscope as claimed in claim 1, wherein the groove is delimited by a partial surface of the objective lens and a partial surface of an inner wall of the endoscope tube, and a side wall of the groove opposite to the endoscope tube is coated with a light-shielding material.

9. The endoscope as claimed in claim 7, wherein the groove is circular ring-shaped;
at least one arc-shaped lighting source is mounted in the groove; or,
one circular ring-shaped lighting source is mounted in the groove.

10. The endoscope as claimed in claim 9, wherein a plurality of arc-shaped lighting sources are uniformly arranged in the groove.

11. The endoscope as claimed in claim 7, wherein the groove is arc-shaped; and at least one arc-shaped lighting source is mounted in the groove.

12. The endoscope as claimed in claim 1, wherein the edge of the inner surface of the objective lens is uniformly provided with a plurality of arc-shaped grooves, and one arc-shaped lighting source is mounted in each of the plurality of arc-shaped grooves.

13. The endoscope as claimed in claim 1, wherein the endoscope is a disposable rigid endoscope or an electronic endoscope.

14. The endoscope as claimed in claim 1, wherein a minimum inner diameter of the endoscope tube is 3.8 mm, a minimum outer diameter of the endoscope tube is 4.0 mm, and a minimum dimension of the lighting source along a radial direction of the endoscope tube is 0.5 mm.

15. A disposable rigid endoscope, comprising an endoscope tube;

an objective lens, located at one end of the endoscope and at least partially located inside the endoscope tube; and a lighting source, located at the end of the endoscope tube where the objective lens is provided, wherein the lighting source comprises a light-emitting diode (LED) chip and a substrate;

the LED chip is arranged on and fixedly connected to the substrate, and is packaged into the lighting source; and the lighting source is circular ring-shaped or arc-shaped, wherein the LED chip is a semiconductor die, wherein at least two LED chips are arranged on the substrate with a wire connected between the at least two LED chips, and the at least two LED chips, the wire and the substrate are packaged into a circular ring-shaped or arc-shaped package.

\* \* \* \* \*